United States Patent [19]
Bekki et al.

[11] Patent Number: 4,944,758
[45] Date of Patent: Jul. 31, 1990

[54] ARTIFICIAL FINGER JOINT

[75] Inventors: Katsutoshi Bekki; Shigeo Niwa, both of Aichi, Japan

[73] Assignee: NGK Spark Plug Co., Ltd., Aichi, Japan

[21] Appl. No.: 245,255

[22] Filed: Sep. 16, 1988

[30] Foreign Application Priority Data

Sep. 18, 1987 [JP] Japan .......................... 62-141586[U]

[51] Int. Cl.⁵ .......................... A61F 2/42; A61F 2/32
[52] U.S. Cl. .......................................... 623/21; 623/18
[58] Field of Search ..................................... 623/18–21

[56] References Cited

U.S. PATENT DOCUMENTS

| | | | | |
|---|---|---|---|---|
| 3,760,427 | 9/1973 | Schultz | .............................. | 623/21 X |
| 3,869,729 | 3/1975 | Attenborough | ...................... | 623/20 |
| 3,918,101 | 11/1975 | Lagrange et al. | ...................... | 623/20 |
| 4,059,854 | 11/1977 | Laure | ..................................... | 623/20 |
| 4,755,185 | 7/1988 | Tarr | ................................... | 623/21 X |

Primary Examiner—Ronald Frinks
Attorney, Agent, or Firm—Finnegan, Henderson, Farabow, Garrett, and Dunner

[57] ABSTRACT

An artificial joint comprising a first member including a butt portion located at one end of the first member and having an internal opening and a long guide groove extending to the opening and a second member in contact with the butt portion of the first member and including an expanded portion at one end of the second member. The expanded portion is fitted in the internal opening of the first member. A projection along both sides of the long guide groove prevents the expanded portion from separating from the internal opening except at prescribed positions of the first and second members. The long guide groove guides the movement of the second member as it bends relative to the first member in a prescribed direction.

10 Claims, 3 Drawing Sheets

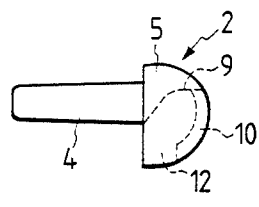
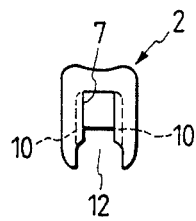
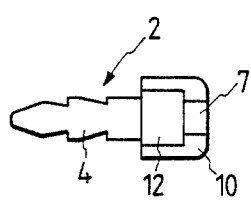
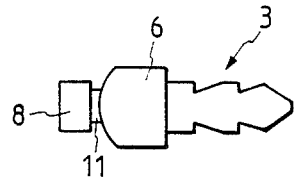
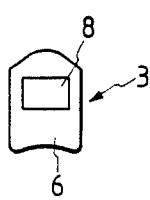
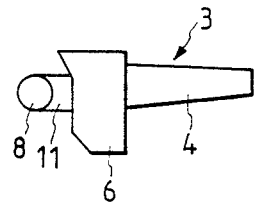
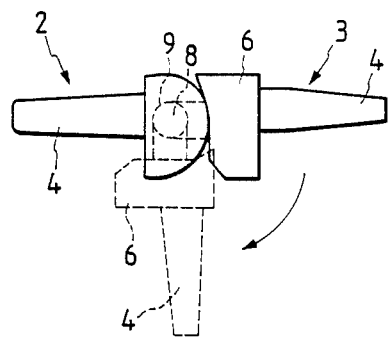

ARTIFICIAL FINGER JOINT

BACKGROUND OF THE INVENTION

1. Field of the Invention

The present invention relates to the improvement of an artificial finger joint for fields such as orthopedics.

2. Description of the Related Art

One conventional artificial finger joint used as a substitute for a damaged natural finger joint comprises a member having an embedded portion at one end of the member and a jut at the other end of the member, and another member having an embedded portion at one end of the member and a recess at the other end of the member. The members are coupled to each other by fitting the jut in the recess, so that the members can be turned relative to each other. Since the two members are coupled to each other in a manner so that they can be turned relative to each other, problems of separation and irregular movement arise. The mutually coupled portions of the members are prone to moving irregularly or separating from each other due to a clearance which develops between the members during use of the joint or a clearance which is present between the members by design in order to render them turnable relative to each other.

Another conventional artificial finger joint used as a substitute for a damaged natural finger joint also comprises a member having an embedded portion at one end of the member and a jut at the other end of the member, and another member having an embedded portion at one end of the member and a recess at the other end of the member. A vertical groove is provided in the jut of the former member. An attaching material having an elastic fitting portion is tightly fitted in the vertical groove. The two members are coupled to each other by fitting the jut in the recess and using a pin. The central portion of the pin has a groove in which is fitted the elastic fitting portion of the attaching material tightly fitted in the vertical groove of the jut. The members can be turned relative to each other. Due to the construction of this type of artificial finger joint, the number of component parts is larger and the process of manufacturing the joint is complicated. For these reasons, the cost of the joint is high and the efficiency of manufacturing is very low.

SUMMARY OF THE INVENTION

The present invention was made in order to solve the above-mentioned problems of the conventional artificial finger joints.

Accordingly, it is an object of the present invention to provide an artificial finger joint with simple construction and with members that can be bent relative to each other in only a prescribed direction and cannot be separated from each other except in prescribed positions of the members.

Another object of the present invention is to provide an artificial finger joint which permits smooth movement and is simple in construction.

A further object of the present invention is to provide an artificial finger joint with members which cannot be separated from one another except in prescribed positions of the members and which eliminates the need for elastic fittings in artificial finger joints.

The artificial joint of the present invention comprises a first member including a butt portion located at one end of the first member and having an internal opening and a long guide groove extending to the opening; a second member in contact with the butt portion of the first member and including an expanded portion at one end of the second member, the expanded portion fitted in the internal opening of the first member; and a projection along both sides of the long guide groove preventing the expanded portion from separating from the internal opening except at prescribed positions of the first and second members, the long guide groove guiding the movement of the second member as it bends relative to the first member in a prescribed direction.

BRIEF DESCRIPTION OF THE DRAWINGS

The manner by which the above and other objects are attained will be fully apparent from the following detailed description when considered with reference to the accompanying drawings; wherein:

FIG. 5(A) shows a front view of the first member of an artificial finger joint which is a third embodiment of the present invention;

FIG. 5(B) shows a side view of the first member shown in FIG. 5(A);

FIG. 5(C) shows a bottom view of the first member shown in FIG. 5(A);

FIG. 6(A) shows a plan view of the second member of the artificial finger joint shown in FIG. 5(A);

FIG. 6(B) shows a side view of the second member shown in FIG. 6(A);

FIG. 6(C) shows a front view of the second member shown in FIG. 6(A); and

FIG. 7 shows a front view of the artificial finger joint shown in FIG. 5(A) and FIG. 6(C).

DETAILED DESCRIPTION OF THE PREFERRED EMBODIMENTS

The artificial finger joint of the present invention includes a first member including a semicircular butt portion located at one end of the member and having an internal opening and a long guide groove communicating with the opening, and a second member including an expanded portion located at one end of the member and fitted in the internal opening of the first member so that the expanded portion can be smoothly slid back and forth in only a prescribed direction while being guided along the long guide groove of the first member. A projection is provided along the side edges of the long guide groove of the first member. The second member is engaged with the projection of the first member at the rear end of the expanded portion of the second member so that the first and the second members can be moved relative to each other in only a prescribed direction along the long guide groove without separating from each other. For that reason, the artificial finger joint can be bent in only the prescribed direction. The first member is provided with a wide opening at the lower or upper part of the long guide groove so that the expanded portion of the second member can be easily fitted into the internal opening of the first member through the wide opening. The first and the second members engaged with each other cannot be separated from each other without taking the expanded portion of the second member out of the internal opening of the first member through the wide opening. Due to the simple construction of the joint of the present invention, the cost of the artificial joint is reduced and the efficiency of manufacturing the joint is improved.

The embodiments of the present invention are described in detail with reference to the attached drawings.

Figure 1A:
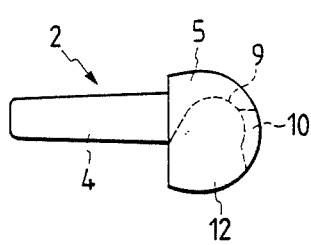
FIG. 1(A) shows a front view of the first member of an artificial finger joint which is a first embodiment of the present invention.
Figure 1B:
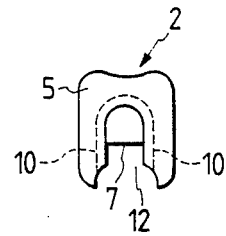
FIG. 1(B) shows a side view of the first member shown in FIG. 1(A)
Figure 1C:
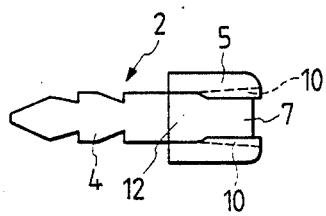
FIG. 1(C) shows a bottom view of the first member shown in FIG. 1(A)
Figure 3A:
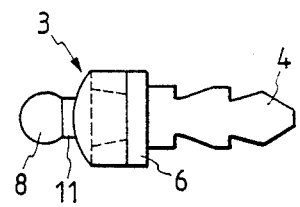
FIG. 3(A) shows a top view of the second member of each of the artificial finger joints mentioned above.
Figure 3B:
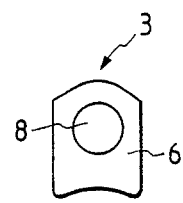
FIG. 3(B) shows a side view of the second member.
Figure 3C:
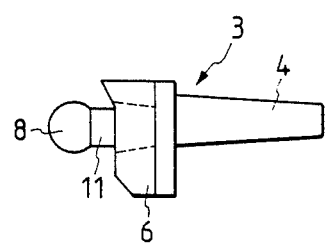
FIG. 3(C) shows a front view of the second member.
Figure 4:
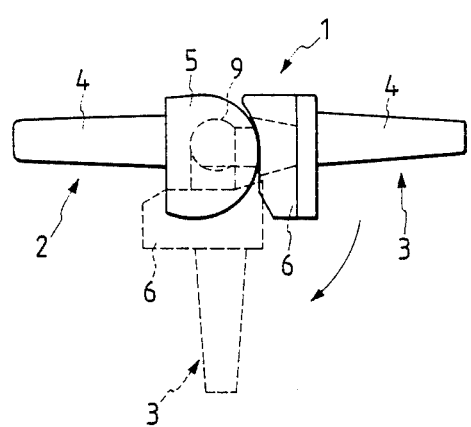
FIG. 4 shows a front view of each of the artificial finger joints mentioned above.

The first embodiment of an artificial finger joint in accordance with the present invention includes a first member 2 as shown in FIGS. 1(A), 1(B) and 1(C) and a second member 3 as shown in FIGS. 3(A), 3(B) and 3(C) associated as illustrated in FIG. 4.

FIGS. 1(A), 1(B) and 1(C) show the first member 2 including an embedded portion 4, which is embedded in a bone, and semicircular butt portion 5 having an internal opening 9 and a long guide groove 7 along which a separation preventive projection 10 is provided.

FIGS. 3(A), 3(B) and 3(C) show the second member 3 including an embedded portion 4, which is embedded in another bone, a second butt portion 6 having a protrusion on the upper surface, an expanded portion 8 and a constricted portion 11. The expanded portion 8 is located at one end of the second member 3 and is movably fitted in the internal opening 9 of the first member 2. The constricted portion 11 is located between the butt portion 6 and the expanded portion 8 so that the constricted portion slides on the separation preventive projection 10 of the first member 2 along the long guide groove 7.

As shown in FIGS. 1(A), 1(B) and 1(C), the long guide groove 7 and the internal opening 9 are provided in the semicircular butt portion 5 of the first member 2. An insertion opening 12, which is wide enough to fit the expanded portion 8 of the second member 3 into the internal opening 9 of the first member 2 through the insertion opening, is provided in the first member under the long guide groove 7. The separation preventive projection 10 extends along both side edges of the long guide groove 7, and is engaged with the constricted portion 11 of the second member 3 to guide the second member along the long guide groove so that the second member can be moved back and forth in only a prescribed direction, relative to the first member 2, without separating therefrom, as shown by an arrow in FIG. 4.

As shown in FIG. 4, the curved surface of the butt portion 6 of the second member 3 contacts that of the semicircular butt portion 5 of the first member 2 so that the artificial finger joint 1 can be smoothly bent as shown by the arrow in FIG. 4.

Figure 2A:
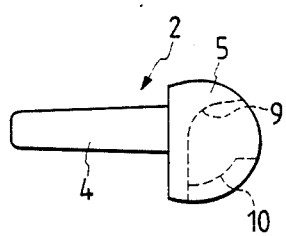
FIG. 2(A) shows a front view of the first member of an artificial finger joint which is a second embodiment of the present invention.
Figure 2B:
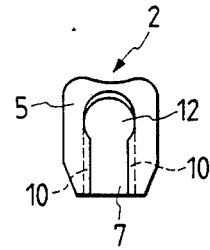
FIG. 2(B) shows a side view of the first member shown in FIG. 2(A)
Figure 2C:
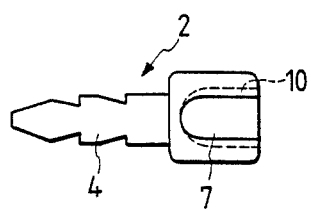
FIG. 2(C) shows a bottom view of the first member shown in FIG. 2(A)

The second embodiment of an artificial finger joint in accordance with the present invention includes a first member 2 as shown in FIGS. 2(A), 2(B) and 2(C) and a second member 3 as shown in FIGS. 3(A), 3(B) and 3(C) associated as illustrated in FIG. 4. The second embodiment includes the same second member as the artificial finger joint of the first embodiment. In the first member 2 for the second embodiment, an insertion opening 12 is provided at the upper part of a long guide groove 7 so that the expanded portion 8 of the second member is fitted into the internal opening 9 of the first member through the insertion opening. The constricted portion 11 of the second member is engaged with the separation preventive projection 10 of the first member 2, which is provided along the long guide groove 7 of the first member. As a result, the second member is guided along the long guide groove 7 of the first member 2 so that the second member can be moved back and forth in only a prescribed direction, relative to the first member, without separating therefrom, as shown by the arrow in FIG. 4.

FIGS. 5(A)-(C), 6(A)-(C) and 7 show an artificial finger joint which is a third embodiment of the invention. The artificial finger joint comprises a first member 2 having an internal opening 9 and an insertion opening 12 as shown in FIGS. 5(A), 5(B) and 5(C), and a member 3 having an expanded portion as shown in FIGS. 6(A), 6(B) and 6(C). The cross-section of the insertion opening 12 of the first member 2 and that of the expanded portion 8 of the second member 3 are quandrangularly shaped to correspond to each other.

As shown in FIG. 7, the expanded portion 8 of the second member 3 is fitted into the internal opening 9 of the first member 2 through the insertion opening 12, and the constricted portion 11 of the second member is engaged with separation preventive projection 10 provided in the first member along the long guide groove 7. As a result, the second member 3 is guided along the long guide groove 7 of the first member 2 so that the second member can be moved back and forth in only a prescribed direction, relative to the first member, without separating therefrom, as shown by an arrow in FIG. 7.

Thus, an artificial finger joint in accordance with the present invention is a joint of simple construction comprising two members, which permits smooth motion as the expanded portion of the second member slides in the internal opening of the butt portion of the first member. The separation preventive projection is provided along the long guide groove and engages the second member, restricting the motion of the second member so that it may move in a prescribed direction only relative to the first member and preventing the members from separating except at prescribed positions of the members. Since structural features of the members of the joint of present invention solve the problem of separation of the members in an artificial joint, the present invention eliminates the need for elastic fittings found in conventional artificial finger joints in order to prevent separation. Thus, the present invention has the resultant advantage of low cost manufacturing.

What is claimed is:
1. An artificial finger joint comprising:
 a first member adapted for fixation to a first bone including a butt portion shaped generally as a single ball located at one end of said first member and having a socket type structure with an internal opening and a long guide groove extending to said internal opening;
 a second member adapted for fixation to a second bone in contact with the butt portion of said first member and including an expanded portion at one end of said second member and a generally cylindrical portion, adjacent the expanded portion along the member, said expanded portion formed as an integral part of said second member and fitted in said internal opening of said first member;

a thin projection along both sides of said long guide groove preventing said expanded portion from separating from said internal opening except at prescribed positions of said first and second members, said long guide groove being adapted for guiding the movement of said second member as it bends relative to said first member in a prescribed direction and said cylindrical portion being adapted for sliding on the projection along the long guide groove; and an insertion opening in said butt portion for receiving said expanded portion and leading to said internal opening of said butt portion, said insertion opening being located below an upper side of said butt portion.

2. The artificial joint according to claim 1, wherein said butt portion of said first member is a semicircular configuration.

3. The artificial joint according to claim 2, wherein said second member further includes a second butt portion with a curved surface in contact with the semicircular butt portion of said first member.

4. The artificial joint according to claim 1, wherein said cylindrical portion is a constricted portion.

5. The artificial joint according to claim 1, wherein said insertion opening is wide enough to fit the expanded portion of said second member into the internal opening of said first member.

6. The artificial joint according to claim 5, wherein said insertion opening is located at the upper end of said long guide groove.

7. The artificial joint according to claim 1, wherein said expanded portion of said second member has a quadrangle for a cross-section.

8. The artificial joint according to claim 5, wherein said insertion opening is shaped as a quadrangle.

9. An artificial joint comprising:
a first member adapted for fixation to a first bone including a butt portion shaped generally as a single ball located at one end of said first member and having a socket type structure with an internal opening and a long guide groove extending to said internal opening;
a second member adapted for fixation to a second bone in contact with the butt portion of said first member and including an expanded portion at one end of said second member, said expanded portion fitted in said internal opening of said first member;
a thin projection along both sides of said long guide groove preventing said expanded portion from separating from said internal opening except at prescribed positions of said first and second members, said long guide groove guiding the movement of said second member as it bends relative to said first member in a prescribed direction;
an insertion opening in said butt portion for receiving said expanded portion and leading to said internal opening of said butt portion, said insertion opening being wide enough to fit the expanded portion of said second member into the internal opening of said first member and being located below an upper side of said butt portion and below said long guide groove.

10. An artificial joint comprising:
a first member adapted for fixation to a first bone including a butt portion shaped generally as a single ball located at one end of said first member and having a socket type structure with an internal opening and a long guide groove extending to said internal opening;
a second member adapted for fixation to a second bone in contact with the butt portion of said first member and including an expanded portion at one end of said second member, said expanded portion fitted in said internal opening of said first member;
a thin projection along both sides of said long guide groove preventing said expanded portion from separating from said internal opening except at prescribed positions of said first and second members, said long guide groove guiding the movement of said second member as it bends relative to said first member in a prescribed direction; and
an insertion opening in said butt portion for receiving said expanded portion and leading to said internal opening of said butt portion, said insertion opening being located below an upper side of said butt portion; and wherein
said butt portion of said first member is a semicircular configuration;
said second member further includes a second butt portion with a curved surface in contact with the semicircular butt portion of said first member; and
said second butt portion includes a protrusion on the upper surface.

* * * * *